United States Patent
Michalson et al.

(10) Patent No.: US 6,673,951 B1
(45) Date of Patent: Jan. 6, 2004

(54) PROCESS FOR CATALYTICALLY HYDROGENATING PHYTOSTEROLS

(75) Inventors: Erik T. Michalson, Charles City, IA (US); James D. Devore, Charles City, IA (US)

(73) Assignee: Salsbury Chemicals, Inc., Charles City, IA (US)

( * ) Notice: Subject to any disclaimer, the term of this patent is extended or adjusted under 35 U.S.C. 154(b) by 0 days.

(21) Appl. No.: 10/229,413

(22) Filed: Aug. 29, 2002

(51) Int. Cl.[7] .................................................. C07J 9/00
(52) U.S. Cl. ....................... 552/544; 502/253; 502/329; 502/250; 502/252; 562/512; 562/606; 562/513
(58) Field of Search .......................... 552/544; 502/253, 502/329, 250, 252; 562/512, 606, 513

(56) References Cited

U.S. PATENT DOCUMENTS 5,616,531 A * 4/1997 Feldhauser et al. .......... 502/253
6,147,235 A * 11/2000 Helminen et al. .......... 552/544

FOREIGN PATENT DOCUMENTS

GB          2316328       *  2/2002

* cited by examiner

Primary Examiner—Sabiha Qazi
(74) Attorney, Agent, or Firm—Richard J. Hammond

(57) ABSTRACT

The present invention provides a process for catalytically hydrogenating unsaturated phytosterol compounds. The catalyst used for such hydrogenation is an alumina-supported transition metal selected from the group consisting of nickel, palladium, platinum, ruthenium, rhodium and mixtures thereof. The process involves the following steps.

Admixing a solvent, the alumina-supported transition metal catalyst and a material that contains at least one unsaturated phytosterol compound and hydrogenating said admixture for a time and at a temperature and pressure sufficient to cause the hydrogenation of the material that contains at least one of said unsaturated phytosterol compounds; separating said alumina-supported transition metal catalyst from said mixture; admixing with a new solvent a material that contains at least one unsaturated phytosterol compound and hydrogenating said admixture for a time and at a temperature and pressure sufficient to cause the hydrogenation of the material that contains at least one unsaturated phytosterol compound; and separating the alumina-supported transition metal catalyst from the hydrogenated mixture. Such separated catalyst may be used again for subsequent hydrogenations of materials that contain phytosterol compounds.

The hydrogenation process disclosed herein can also be applied to the hydrogenation of fatty acids derived from unsaturated phytosterols, e.g., tall oil, vegetable oil and their distillation products.

6 Claims, No Drawings

PROCESS FOR CATALYTICALLY HYDROGENATING PHYTOSTEROLS

FIELD OF INVENTION

This invention relates to a process for the catalytic hydrogenation of plant-based steroid compounds. More particularly, this invention relates to the metal-catalyzed hydrogenation of phytosterols and to the recovery and regeneration of the metal catalyst species used in such metal-catalyzed hydrogenation.

BACKGROUND OF THE INVENTION

Steroids are macromolecular organic compounds that, structurally, comprise a cyclopentanephenanthrene skeleton. Many of these compounds are alcohols and are identified as sterols. When combined to form esters, these compounds are called "cerides".

Cholesterol, a sterol, has been known for some time. It has been reputed as being involved in the formation of biliary calculi, a theory which has been confirmed by proof of its involvement in circulatory disorders, and more particularly in the hardening of the arteries.

Nonesterified cholesterol is the main constituent of fatty substances having an animal origin. These animal fats are present in most of our foodstuffs and constitute an important source of cholesterol. When ingested in excess, they may breakdown, releasing cholesterol and the fatty acids which, in turn, may cause serious cardiovascular diseases.

However, fatty substances having a plant origin do not contain cholesterol, but instead comprise a mixture of cholesterol-like materials called phytosterols, i.e., they are unsaturated, plant-based compounds comprising the cyclopentanephenanthrene skeleton. The best known of such compounds include: stigmasterol, sitosterol and ergosterol.

The structure of the molecule on which the animal and plant steroids is based is shown below:

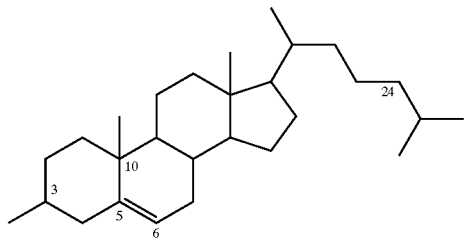

The C 3 carbon atom is hydroxyl-substituted. The carbon atom at position 10 bears a methyl group.

The stereochemistry of the substituents at C 3 and C 10 is important. The steroid ring is a planar structure and, for cholesterol, the two groups at C 3 and C 10 lie above the plane of the ring, i.e., they are in the β conformation. The hydrogen atom at position C 6 (see the double bond between C 5 and C 6) lies below the plane, i.e., it is in the a position. Cholesterol's phytosterol look-alike, sitosterol, is substantially identical to cholesterol but, in addition bears an ethyl group at C 24.

In the reduction of these steroid-based structures, it is important to retain the stereochemical conformation of the starting material. Such reductions have typically been carried out with varying degrees of success, using hydrogen in the presence of supported metallic catalysts. See, for example, U.S. Pat. No. 3,865,853. Such catalysts include iron, cobalt, nickel, palladium, platinum, copper, silver and gold.

As disclosed in U.S. Pat. No. 6,147,235, steroids have been hydrogenated in the presence of catalytic amounts of nickel black, Raney Nickel, and nickel metal embedded in inorganic supports. However, these catalysts have not proven sufficiently selective for hydrogenation of the steroid double bond.

The '235 patent also shows that steroids have been hydrogenated using noble metal catalysts, principally platinum and palladium. According to this patent, these catalysts have been supported on inorganic substrates, on carbon or used as metal blacks. The best conversions have been obtained when such noble metal catalysts are bound to activated carbon. The noble metal of choice is palladium and one of the most successful of the catalyst species has been shown to be palladium on carbon.

However, prior art catalysts used for the reduction of steroids have proven to be disadvantageous because of difficulties of separation of the catalyst powder from the reaction mass after the hydrogenation process, the inflammability of the catalyst and the catalyst is not recyclable.

As shown on U.S. Pat. No. 6,147,235 palladium bound to an organic substrate (a polyolefin or halo polyolefin) also has been used successfully. The process for manufacturing such a catalyst is difficult and the expense of such a catalyst species has limited its use.

SUMMARY OF THE INVENTION

It is the object of the present invention to provide a process for catalytically hydrogenating unsaturated phytosterol compounds. The catalyst used for such hydrogenation is an alumina-supported transition metal selected from the group consisting of nickel, palladium, platinum, ruthenium, rhodium and mixtures thereof.

The process of the present invention is as follows.

An admixture of a solvent, an alumina-supported transition metal catalyst and a material comprising at least one of the unsaturated phytosterol compounds is first formed. This admixture is hydrogenated for a time and at a temperature and pressure sufficient to cause the hydrogenation of at least one of said unsaturated phytosterol compounds.

The alumina-supported transition metal catalyst is next separated from the reaction (the hydrogenated) mixture that was first formed. This separated alumina-supported transition metal catalyst is then admixed with a new mixture containing a solvent and a material comprising at least one unsaturated phytosterol compound. The resulting reaction mixture is hydrogenated for a time and at a temperature and pressure sufficient to cause the hydrogenation of at least one of said unsaturated phytosterol compound. The alumina-supported transition metal catalyst is then separated from the hydrogenated mixture. It may be used again for subsequent hydrogenations of unsaturated phytosterol compounds.

The hydrogenation process disclosed herein can also be applied to the hydrogenation of fatty acids derived from phytosterols, e.g., tall oil, vegetable oil and their distillation products.

DESCRIPTION OF THE PREFERRED EMBODIMENTS

In the present invention, the process described can be applied to any material comprising a phytosterol compound or compounds, i.e., any plant-based, unsaturated steroid compound or compounds, including those plant-based compounds that are unsaturated fatty acids and triglycerides, e.g., lineolic, linolenic and oleic acids. Such compounds are non-hormonal steroids which are, for example, wood-based unsaturated steroids that are found in the neutral fraction of pulping or in soy. Specifically these compounds may include campesterol, stigmasterol, sitosterol, ergosterol and the like as well as their cleavage products, i.e., campesterene, sitosterene and the like.

The hydrogenation process, sometimes referred to herein as a "reduction" process, is carried out by employing a metal catalyst species that is a transition metal bound to alumina as a support usually in the form of a powder or pellet although the actual form of the material is not important. Typical transition metals of use in the present invention include nickel, platinum, palladium, ruthenium or rubidium, preferably palladium. The metals are present in the catalyst species in a concentration of from about 1% to about 20%, preferably from about 5% to about 10%. These catalysts are readily available commercially.

In the process of the present invention, the phytosterol (or the fatty acid or triglyceride) and the catalysts species are admixed with or without a solvent, preferably with a solvent. Such solvent is one that is inert to the reactants and to the process, i.e., its function is to provide a medium to enhance the absorption of the phytosterol compounds onto the catalyst site and facilitate the contact of such with hydrogen, which is typically introduced into the reaction mass in the gaseous form. The solvents of particular use in this invention are organic and include the lower alkyl aliphatic alcohols, e.g., methanol, ethanol, i-propyl alcohol, etc., the alkanes, e.g., hexane, heptane, etc., and cycloalkanes, e.g., cyclohexane.

Temperatures, pressures and reaction times for carrying out the process of the present invention are typically sufficient to achieve the reduction of the unsaturated phytosterol compounds (or the fatty acids or triglyceride). Such temperatures and pressures are preferably from about 25° to about 100° C. (most preferably about 25° to about 80° C.) and about 50 to about 200 psig.

Unlike the prior art catalytic process for the reduction of unsaturated phytosterol compounds, the process of the present invention reuses the catalyst that was employed in the first hydrogenation step without any treatment of the catalyst species other than the removal of it from the hydrogenated reaction mixture. Such removal is typically accomplished by filtration, with the catalyst species remaining in the filter as a residue. The filtrate, of course, contains the reduced phytosterol products. However, other conventional procedures are possible for recovering the catalyst species, e.g., decantation. The catalyst species is typically recovered while still wet with solvent. It can then be used, as such, in the next reduction of a new batch of material comprising unsaturated phytosterols. However, the recovered catalyst species can be washed a number of times with a suitable phytosterol-dissolving solvent to remove any organic residues clinging to the catalyst species and subsequently reused in the hydrogenation of a new batch of material comprising unsaturated phytosterols.

The following examples are intended to illustrate the process of the present invention and are not to be regarded as limiting such process in a any way.

EXAMPLES

Example 1

A one liter autoclave was charged with 130 g isopropyl alcohol, 50 g "wood sterol" having the following analysis: campesterol (including campestanol) 9.2%; β-sitosterol (including 14.4% β-sitostanol) 88.7%; α-sitosterol 0.0%; artenols 0.9%; ash (@ 600° C. 0.43%; solids content 97.6%; melting range 139–140° C. Under a nitrogen purge, 0.75 g of 5% palladium on alumina (Englehard Corporation C3683, Lot FC00089) was then slurried into this mixture with 2.0 g deionized water. Catalyst transfer was completed by rinsing the transfer vessel with 1.0 g deionized water and then with 70 g isopropyl alcohol.

The autoclave was sealed, purged with nitrogen, pressurized with hydrogen to 120 psig, heated to 80° C. (±2° C.) and stirred at 600 rpm for 3 hours.

At the end of the stirring period, the autoclave was cooled to <70° C. and purged with nitrogen. The contents of the autoclave were heated to 82–83° C. and transferred to a 1 liter beaker, followed by a hot isopropyl alcohol rinse.

The contents of the beaker, at about 82° C., were filtered leaving the wet catalyst as a residue in the filter and the hydrogenated product as filtrate.

The hydrogenated product was cooled to 0–5° C. and crystallized upon cooling. It was filtered and the residue dried in a convection oven (house vacuum at 80° C.) overnight. The amount of dried crystallized solid recovered was 40.78 g. The composition of this product is reported in the Table below.

The wet catalyst (note—the dried, activated catalyst may ignite spontaneously) was recovered in 1.97 g, the difference between the original amount of catalyst (1 g) and this amount due to product that adhered to the wet catalyst after the reduction. It was not washed out.

Example 2

The above process was repeated, using 0.5 g of the catalyst species. The amount of catalyst recovered was 0.7 g. The details of this Example are reported in the Table below.

Examples 3 and 4

The above procedure was repeated. However, the catalyst recovered from Example 1 and Example 2 was reused. The details of these Examples are reported in the Table below.

TABLE

Temperatures are in degrees centigrade, pressures in psig, "Camp" is campestanol and "Sito" is Sitostanol.

| Phytosterols | Catalyst | | Hydrogenation | | Conversion | | Product |
|---|---|---|---|---|---|---|---|
| amount (g) | fresh | recycle | Temp | Pressure | % Camp | % Sito | amount (g) |
| 50 | 1 g | | 65–74 | 50–62 | 86.2 | 95.87 | 40.78 |
| 50 | 0.5 g | | 75–82 | 90–110 | 93.79 | 97.98 | 41.84 |
| 50 | | 1.1 g | 75–79 | 93–110 | 96.53 | 99.22 | 44.3 |

TABLE-continued

Temperatures are in degrees centigrade, pressures in psig, "Camp" is campestanol and "Sito" is Sitostanol.

| Phytosterols amount (g) | Catalyst fresh | Catalyst recycle | Hydrogenation Temp | Hydrogenation Pressure | Conversion % Camp | Conversion % Sito | Product amount (g) |
|---|---|---|---|---|---|---|---|
| 50* | | 1.0 g | 75–80 | 90–110 | 91.32 | 93.71 | not dry |
| 50* | | 1.19 | 75–80 | 90–100 | 87.2 | 85.96 | 42.99 |

*Sterol content 97.8%; volatiles 1.9%; ash content 0.006%; sulfur 10 mg/kg; lead, 0.05 mg/kg; mercury ,0.025 mg/kg; cadmium, 0.06 mg/kg

We claim:

1. A process for catalytically hydrogenating unsaturated phytosterol compounds, said catalyst being an alumina-supported transition metal selected from the group consisting of nickle, palladium, platinum, ruthenium, rhodium and mixtures thereof comprising
   a) admixing said alumina-supported transition metal catalyst with a material that contains at least one unsaturated phytosterol compound in a solvent for a time and at a temperature and pressure sufficient to hydrogenate said material that contains at least one unsaturated phytosterol compound;
   b) separating said alumina-supported transition metal catalyst from the hydrogenated mixture;
   c) repeating step a) using said separated alumina-supported transition metal catalyst without any treatment of the catalyst other then removal of it from the hydrogenated reaction mixture and a new material that contains at least one unsaturated phytosterol compounds in a solvent; and
   d) separating said alumina-supported transition metal catalyst from the hydrogenated mixture.

2. The process according to claim 1 wherein the catalytic hydrogenation is carried out at a pressure of about 50 to about 200 psig.

3. The process according to claim 1 wherein said temperature of the catalytic hydrogenation is from about 25° to about 100° C.

4. The process according to claim 1 wherein said catalyst is alumina-supported palladium.

5. The process according to claim 4 wherein said catalyst is 5% by weight palladium on alumina.

6. The process according to claim 1 wherein the material that contains at least one unsaturated phytosterol compound is wood-based or soy-based.

* * * * *